United States Patent [19]

Funakoshi et al.

[11] Patent Number: 5,648,462
[45] Date of Patent: Jul. 15, 1997

[54] PEPTIDE PURIFICATION METHOD USING NOVEL LINKER AND SOLID-PHASE LIGAND

[75] Inventors: Susumu Funakoshi, Otsu; Hiroyuki Fukuda, Toyonaka, both of Japan

[73] Assignee: Setsuko Funakoshi, Otsu, Japan

[21] Appl. No.: 379,039

[22] Filed: Jan. 27, 1995

Related U.S. Application Data

[63] Continuation of Ser. No. 44,325, filed as PCT/JP91/01379, Oct. 9, 1991, abandoned.

[30] Foreign Application Priority Data

Oct. 9, 1990 [JP] Japan .................... 2-269640

[51] Int. Cl.$^6$ ................................. A61K 38/04
[52] U.S. Cl. ................ 530/344; 530/334; 530/337; 530/345; 530/336
[58] Field of Search ...................... 530/333, 335, 530/344

[56] References Cited

U.S. PATENT DOCUMENTS 4,304,715  12/1981  Hudson et al. ................. 260/112.5

FOREIGN PATENT DOCUMENTS 2058077  4/1981  United Kingdom .

OTHER PUBLICATIONS

Fujii, *Chem Pharm Bull* 35, 388 (1987).
Funakoshi *Proc Nat'l Acad Sci* 88 6981 1991.
Krieger *Proc Natl Acad Sci* 73 3160 1976.

Krieger, D.E., et al., "Affinity Purification of Synthetic Peptides," *Proc. Natl. Acad. Sci. USA*, 73:3160–3164 (1976).
Fujii, N., et al., "Studies on Peptides. CLV. Evaluation of Trimethylsilyl Bromide as a Hard–Acid Deprotecting Reagent in Peptide Synthesis," *Chem. Pharm. Bull.*, 35:3880–3883 (1987).
Funakoshi, S., et al., "Chemoselective One–Step Purification Method for Peptides Synthesized by the Solid–Phase Technique," *Proc. Natl. Acad. Sci.*, 88:6981–6985 (1991).
Sucholeiki, I., and Lansbury, P.T., Jr., "Affinity Chromatographic Method for the Purification of Water–Insoluble Peptides," *J. Org. Chem.*, 5478–5484.

*Primary Examiner*—David Lukton
*Attorney, Agent, or Firm*—Hamilton, Brook, Smith & Reynolds, P.C.

[57] ABSTRACT

Disclosed is a method of purifying a mature peptide with a free N-terminus group from a mixture of peptides comprising the mature peptide and immature end-capped peptides. The peptides are bound to a solid-phase support and are produced by solid phase synthesis. The mixture is contacted with a linker comprising a functional group at each terminus. The functional group at one terminus has the structure $-SO_2-CH_2-CH_2-X$, wherein X is an activated carbonate group which reacts selectively with N-terminus of the mature peptide to form a urethane linkage. The functional group at the other terminus is a thiol protected with an acid labile group. After cleaving the peptides from the solid support and thiol protecting group with acid, the mature peptide is separated from the mixture by forming a covalent bond between the liberated thiol and a solid support. Treatment with base cleaves the mature peptide from the linker to give a purified mature peptide.

6 Claims, 5 Drawing Sheets

Step 1

●:—COCH₃

⇩ Deprotection treatment

Step 2

6M Guanidine-HCl containing 0.4M Tris-HCl buffer (pH7.5)

Step 3

Step 4  1) 5%NH₄OH  2) 50%AcOH

PEPTIDE PURIFICATION METHOD USING NOVEL LINKER AND SOLID-PHASE LIGAND

RELATED APPLICATIONS

This application is a continuation of application Ser. No. 08/044,325 filed Apr. 7, 1993 now abandoned, which is a continuation-in-part of PCT/JP91/01379 filed Oct. 9, 1991 designating the United States which claimed priority to Japan 269,640 filed Oct. 9, 1990.

FIELD OF THE INVENTION

The present invention relates to a method for purifying a peptide produced by solid-phase synthesis, and relates to a linker and a solid-phase ligand for bonding the linker for this purification method. More particularly the invention relates to a method for performing a one-step purification of peptides, synthesized by a solid-phase method, with high accuracy and high yield, and relates to the linker and the solid-phase ligand for bonding the linker used for this purification.

BACKGROUND OF THE INVENTION

Peptides and proteins are biological molecules existing normally in organisms. The elucidation of physiological activities and of mechanisms these biological molecules are of much interest to the fields of biochemistry, physiology and medicine. The synthesis of peptides or proteins having specific amino acid sequences has increased due to the use of automated peptide synthesizers. Studies In the above mentioned fields are expected to show sharp progress, if peptides or proteins having specific amino acid sequences can be synthesized with higher purities. However, present peptide synthesis methods produce a relatively large number of impurities, as well as target compound. Therefore all important objective of a solid-phase peptide synthesis method is to recover the target peptide alone from impurities with high speed and high yield.

Gel flirtation, high-performance liquid chromatography, and combination thereof are presently for the purification of peptides or proteins synthesized by a solid-phase method (R. B. Merrifield, J. Am. Chem. Soc., 85, 2149 (1963)). For some special peptides and proteins, affinity chromatography may be an effective purification method, but not a perfect one. The reason is that some of the amino acid deleted peptides may have an affinity (even a low degree) for the supports used in affinity chromatography, the amino acid deleted peptides being synthesized as impurities during the solid-phase synthesis as part of the resultant peptide mixture.

The peptides are synthesized by a step-wise elongation. For example, in case of condensation of a 50 residue peptide with the condensation reaction yield of 99%, the theoretical synthetic yield reaches to 60%. Condensation reaction yield over 99% can not always be obtained since the condensation reaction depends on the sequence of peptides. As a result, amino acid deleted peptides pile up as impurities by incomplete condensation reactions.

A capping by acetic anhydride is performed after every condensation reaction to terminate further elongation of peptide chains of a non-target sequence and to avoid further production of amino acid deleted peptides. After the coupling of the final amino acid, only the peptide having a target amino acid sequence will have an amino group at its N-terminus.

Several reports on purification methods using the N-terminus amino group have been published. (See, for example, R. Camble, R. Garner and G. T. Young, Nature (London), 217, 247 (1968); K. Suzuki, Y. Sasaki and N. Endo, Chem. Pharm. Bull., 24, 1 (1976); D. S. Kemp and D. G. Roberts, Tetrahedoron Lett., 4269 (1975); T. Weiland, C. Birr and H. Wissenbach, Angew. Chem., Int. Ed., Engl., 8, 764 (1969); H. Wissman and R. Geiger, Angew. Chem., Int. Ed., Engl., 9, 908 (1970); R. B. Merrifield and A. E. Bach, J. Org. Chem. 43, 4808 (1975); T. J. Lobl, R. M. Deibel and A. W. Yen, Anal. Biochem., 170, 502 (1988); H. Ball, C. Grecian, S. B. H. Kent and P. Mascagni, in "Peptides", J. E. Rivier and G. R. Marshall, Eds., ESCOM, Leiden 1990 pp 435). However, none of these methods has been able to achieve effective one-step separation, instead complicated separation processes are required.

Another method has been developed in which the target peptide alone is absorbed to a phenyl-mercury column by attaching cysteine-methionine to the N-terminus of the synthesized peptide, and using the SH group of the cysteine. Subsequent to the separation, the methionine-peptide bond is cleaved by BrCN to yield the target peptide. (D. E. Krieger, B. W. Erikson and R. B. Merrifield, Proc. Natl. Acad. Sci. U.S.A., 73, 3160 (1976)) However, this method has a limitation of being not applicable to peptides containing methionine.

SUMMARY OF THE INVENTION

An objective of this invention is to offer a method for purifying peptides made by solid-phase synthesis, and a linker and a solid-phase ligand for bonding the linker used therein so that one-step purification with high-accuracy and high-yield can be performed.

The above objective is achieved by a purification method comprising chemically and selectively isolating a target mature peptide having an amino acid group at the terminus from a mixture of mature target peptide and the end-capped immature amino acid deleted peptides by immobilization to solid-phase ligand via the linker having two functional groups at the termini.

The above objective is also achieved by a purification method for synthesized peptide comprising:

a) after adding the final amino acid for a solid-phase peptide synthesis, adding a linker to the solid-phase to which both a mature target peptide with an amino group at a terminus and immature peptides end-capped by an acylating agent such as acetic anhydride or propionic anhydride acid have been bound, thereby selectively modifying the mature peptide with the linker, wherein the linker has at one terminus a functional group which is able to form a bond with the N-terminus of the mature peptide, the bond being stable to the deprotection reaction of the opposite terminus site of the linker treated later under acidic condition and being specifically cleaved under another condition, and wherein the opposite terminus site of the linker is able to be converted into another active functional group by the deprotection reaction;

b) dissociating the mature peptide and the immature peptides from the solid-phase support by the cleavage reaction performed as the final process of the peptide synthesis;

c) contacting the resultant freed peptide mixture of above step b) with a solid-phase ligand, and thereby selectively immobilizing the mature peptide to the solid-phase ligand via the linker, wherein the solid-phase ligand is modified by a compound which has a functional group capable of forming a stable bond with the functional group of the opposite terminus of the linker produced by the deprotection reaction of the opposite terminus site of the linker; and d) exposing the mature peptide immobilized ligand of above step c) to said another condition under which the bond between the mature peptide and the linker is selectively cleaved, thereby separating the mature peptide from the linker bound ligand.

A preferred embodiment is to isolate the target mature peptide by the following steps:

a) after introducing the final amino acid for a solid-phase peptide synthesis, adding a linker to the solid-phase to which both a mature target peptide with an amino group at a terminus and immarture end-capped peptides have been bound, thereby selectively modifying the mature peptide with the linker, wherein the linker has at one terminus a functional group which is able to form a bond with the N-terminus of the mature peptide, the bond being stable to the deprotection reaction of the opposite terminus site of the linker treated later under an acidic condition and also being specifically cleaved under an alkaline or basic condition, and wherein the opposite terminus site of the linker is able to be converted into an SH group by the deprotection reaction;

b) dissociating the mature peptide and the immature peptides from the solid-phase support by the cleavage reaction performed as the final process of the peptide synthesis;

c) contacting the resultant freed peptide mixture of step (b) step with a solid-phase ligand, and thereby selectively immobilizing the mature peptide to the solid-phase ligand via the linker, wherein the solid-phase ligand is modified by a compound immobilized thereon and which has a functional group capable of forming a stable bond with the SH-group of the opposite terminus of the linker produced by the deprotection reaction of the opposite terminus site of the linker; and d) exposing the mature peptide immobilized ligand of step (c) alkaline condition under which the bond between the mature peptide and the linker is cleaved selectively, thereby separating the mature peptide from the linker-bound ligand.

Another embodiment of the method is to isolate the mature target peptide by the following steps:

a) after introducing the final amino acid for a solid-phase peptide synthesis, adding a linker to the solid-phase to which both a mature target peptide with an amino group at a terminus and immature end-capped peptides have been bound, thereby selectively modifying the mature peptide, wherein the linker has at one terminus a carbonate group which can be converted to a urethane bond reacting with the N-terminus of the target peptide, the urethane bond being stable to the deprotection reaction of the opposite terminus site of the linker treated later under an acidic conditions and being specifically cleaved under an basic condition, and wherein the opposite terminus site of linker is able to be converted into a thiol group by the deprotection reaction;

b) dissociating the mature peptide and the immature peptides from the solid-phase support by the cleavage reaction performed as the final process of the peptide synthesis, while cleaving a thiol protecting group existing at the opposite terminus site of the linker in order to produce the thiol group;

c) contacting the resultant freed peptide mixture of step (b) with solid-phase ligand under a neutral condition, wherein the solid-phase ligand is modified by a compound selected from the group consisting of iodo- and bromo-substituted aliphatic carboxylic acid derivatives immobilized thereon, thereby selectively immobilizing the mature peptide to the solid-phase ligand via the linker with a stable covalent bond, the covalent bond resulting from deiodination and debromination; and d) exposing the mature peptide immobilized ligand of step (c) alkaline condition in order to effect the beta-elimination reaction on the urethane bond between the mature target peptide and the linker, thereby cleaving the mature peptide from the linker-bound ligand.

A linker having the following structural formula (III) is preferably used for the method of this invention:

$$X-NH-(CH_2)_n-\underset{\underset{O}{\|}}{\overset{\overset{O}{\|}}{S}}-CH_2-CH_2-O-\overset{O}{\underset{\|}{C}}-Y \quad (III)$$

wherein n is an interger of one to four,

X is one of

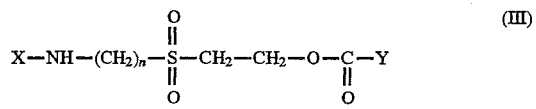   (m = 1~2);

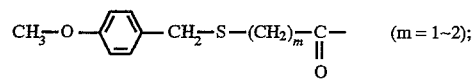 OCH₃; and

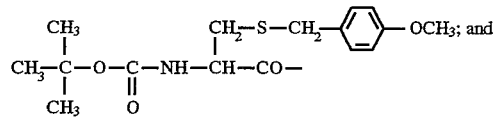 OCH₃;

and

Y is one of

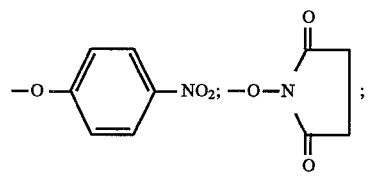

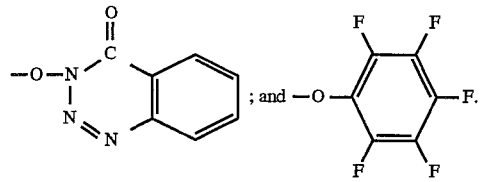

The above linkers can be easily synthesized from intermediates which are represented by the following structural formula (I) or intermediates by the following structural formula (II):

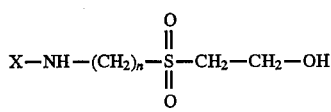

(I)

wherein n is an interger of one to four, X is one of H, hydrochloride thereof (H.HCl),

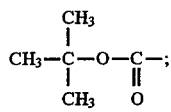

(II)

and

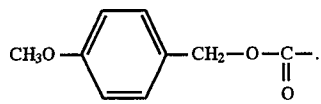

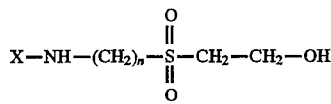

wherein n is an interger of one to four,
X is one of

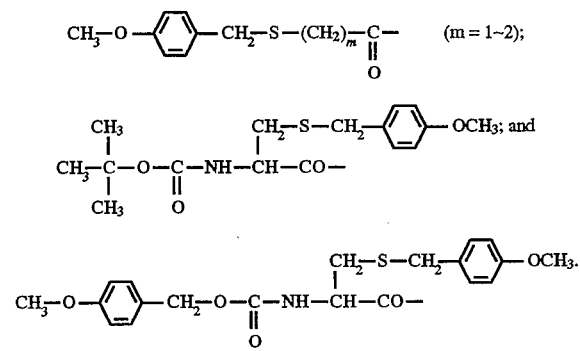

A preferred solid-phase ligand for binding the linker, comprises molecular chains having one of the following structural formulae are bound to the surface thereof:

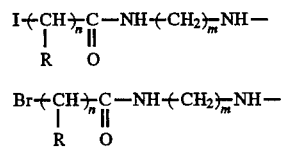

n=1,2, m=2-6, R is H or an alkyl group from one to six carbons.

A method is provided to rapidly and effectively separate the mature target peptide from a mixture of mature peptide and many immature peptides produced in the solid-phase peptide synthesis. The method includes a selective modification of the mature peptide by a linker which has a functional group at one terminus that is capable of bonding with the N-terminus of the mature peptide. This bond is stable to the deprotection reaction of the opposite terminus site of the linker under acidic condition in the post-treatment of the peptide synthesis process and is able to be cleaved specifically under another condition. The opposite site of the linker is able to be converted into another active functional group by the deprotection reaction. When binding the linker to the N-terminus of the mature peptide after the final amino acid coupling step is performed, only the mature peptide has at the opposite terminus the active functional group (resulting in -SH after treated under acidic conditions), post-final deprotection reaction, the active functional group being due to the bound linker. When the mixture is contacted with another solid-phase ligand where a compound having the functional group capable of forming the stable bond with the active functional group of the mature peptide is immobilized thereon, this solid-phase ligand can selectively immobilize the mature peptide alone. This results in the separation of the target mature peptide from the mixture containing immature peptides. The target mature peptide may be cleaved from the linker-bound ligand, when the ligand immobilized to the mature peptide is exposed to other conditions that specifically cleave the urethane bond between the mature peptide and the linker.

The method of this invention can be used to rapidly purify the target mature peptide prepared by the solid-phase synthesis in high yield. Therefore, the method will lead to the elucidation of physiological activities and mechanism of peptides or proteins, and will lead to the rapid development of synthesized.

DETAILED DESCRIPTION OF THE INVENTION

The present invention is hereby described in detail.

Figure 1:
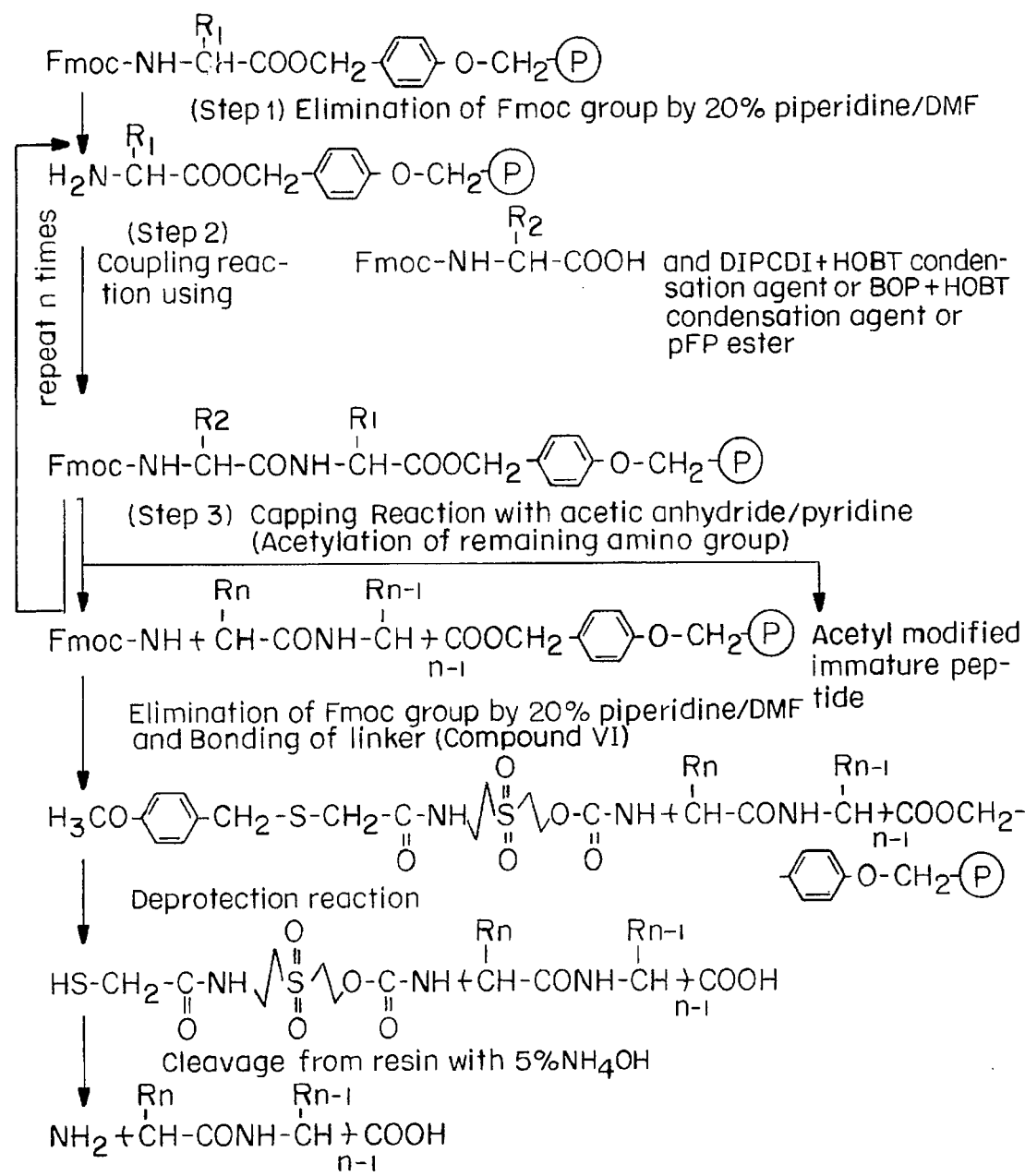
FIG. 1 is a flow chart showing peptide synthesis by Fmoc solid-phase method and subsequent purification of the mature peptide.

FIG. 1 illustrates an embodiment of the method according to this invention for purifying peptides prepared by the Fmoc (9-fluorenylmethyloxycarbonyl) method of solid-phase synthesis.

Peptides are synthesized, as shown in FIG. 1, by the repetition of step 1 to step 3 in the conventional way. Step 1 involves the following procedure: Many first amino residue

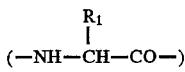

groups whose N-terminus is protected by Fmoc group are bound to solid-phase support beads P; the support beads P are put into a reaction column of a peptide-synthesizer, where the mixed solution of 20% piperidine and dimethylformamide (DMF) is added in order to deprotect the N-terminal Fmoc group.

Step 2 involves: N-terminal Fmoc blocked second amino acid

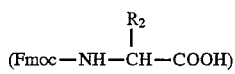

and a condensation agent is added to the column in order to bond the second amino residue group next to the first one bound to the support beads P. A condensation agent, such as N,N'-di-isopropylcarbodiimide (DIPCD)+N-hydroxybenzotriazole (HOBT), Benzotriazole-1-yl-oxy-tris (dimethylamino)-phosphonium hexafluorophoshate (BOP)+ HOBT, or Pentafluorophenylester of these amino acids+ HOBT is used.

Step 3 involves: The chains of the first amino acid that are not bound to the second amino acid should not be elongated in further synthetic steps; the mixture of acetic anhydride/pyridine is added to the column to let the terminus of non-reacted chains end-cap by acetyl-bonding. On the support beads there are two types of peptide chains, i.e., one group contains the first and the second amino acid residues bound together whose N-terminus is protected by an Fmoc group, and the other group contains the first amino residue whose N-terminus is bound to an acetyl group.

The process continues back to step 1. The N-terminal Fmoc group of the chains where the first and the second amino residues are bound together is deprotected. As in step 2, the third amino acid and the condensation agent are added to let the third one bond to the second. The end-capping, as in step 3, results on chains where the third amino acid residue is not bound. Step 1 to step 3 are repeated until the desired number of amino acid residues are bound.

After the coupling of the final amino acid, two types of peptides are bound to the solid support (solid-phase support beads P), namely, the mature target peptide having an amino group at the N-terminus, and the immature peptides having termini modified by an acetyl-group from the capping with acetic anhydride. The target peptide is mixed with many kinds of impurities.

FIG. 1 describes the method to end-cap the terminus of immature peptides with an acetyl group. However, any capping reagent can be used for the capping of the termini of immature peptides with, for example, a propionyl group, a 4-nitrophenyl group, a 2,4-dinitrophenyl group or 2,6-dinitrophenyl group.

For the purification of synthesized peptides, a suitable linker is added to the solid-phase support after the coupling of the last amino acid. The linker should have a functional group at one terminus, which forms with the N-terminus of the mature peptide a bond, such as urethane bond, which is stable under the acidic condition of the deprotection reaction of the opposite terminus site of the linker and cleavable specifically under other conditions, such as basic conditions. The linker should also form an active functional group at the opposite terminus site, when the deprotection reaction is performed.

The Fmoc group (9-fluorenylmethyloxycarbonyl) and the Msc group (methylsulphonylethyloxycarbonyl) (shown below) are suitable amino protection groups because they are stable to the deprotection reaction of the opposite terminus site of the linker performed under acidic conditions and are deleted under basic conditions. These were developed respectively by Carpino et al., (L. A. Carpino and G. Y. Han, J. Am. Chem. Soc., 92, 5478(1970) and J. Org. Chem., 37, 3404 (1972)) and by Tesser et al., (G. I. Tesser and I. C. Balvert-Geers, Int. J. Peptide Protein Res., 7, 295 (1975)).

Fmoc group:

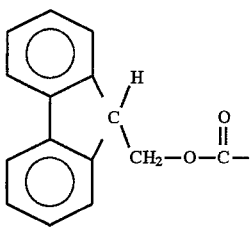

Msc group:

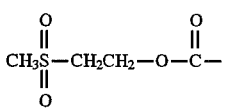

Both amino protection groups can be deleted in a short time, undergoing a β-elimination reaction by an alkaline treatment. Therefore a suitable linker for the present invention can be preferably constructed based on these amino protection groups. The Msc group by Tesser et. al., is more preferred because of the ease of the synthesis and the length of its molecular chain. A preferred linker compound is represented by the structural formula (III) shown below.

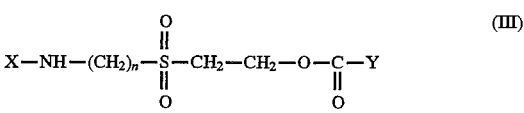

(III)

wherein n is an interger of one to four,
X is one of

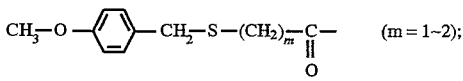

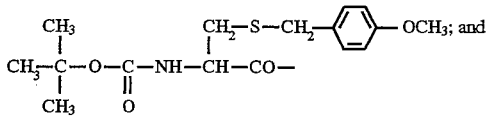

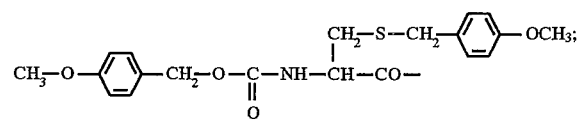

Y is one of

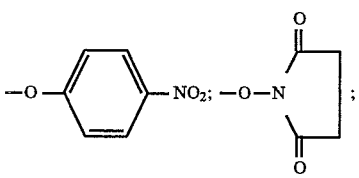

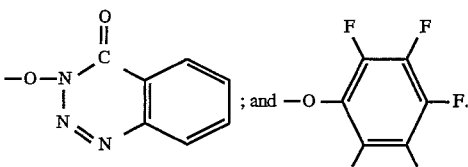

The linker comprises the Msc group as its basic structure, active alkyl or aryl carbonate at one terminus site which can be coupled to the N-terminal amino group of the peptide, and a precursor of a thiol group (SH group) as an active functional group at the opposite terminus site (S is in the state of being protected by a protection group). One terminus site of the linker forms a bond with the N-terminus of the peptide. The bond is stable to any kind of acid used as a deprotection reagent, and is easily cleaved by an alkaline reagent causing a β-elimination reaction, such as 0.2N NaOH (50 w/w % in methanol, 5 sec.) or 5 w/w % NH$_4$OH (50 w/w % in methanol, 5 min.). The SH group at opposite terminus site of the linker reacts with an iodoacetic acid derivative, permitting the formation of a stable thioester type covalent bond under neutral or basic conditions.

The synthetic pathway to the linker represented by structural formula (III) is not subject to any limitation. For example, the linker is preferably synthesized from the intermediate represented by the structural formula (I) involving the Msc group as a basic structure.

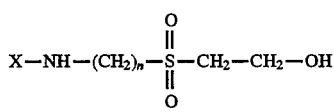
(I)

wherein n is an interger of one to four; X is one of H, hydrochloride thereof (H.HCl),

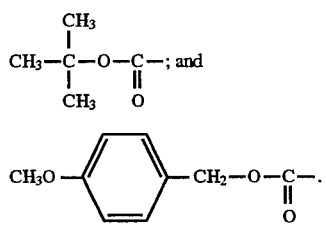

The hydroxyl group at one end of the intermediate represented by structural formula (I) can easily be converted to an active carbonate which can couple with an amino group of a peptide or protein. An amino group or an amino group of the structured formula (I) by a suitable protection group at the other terminus of the intermediate (I) can easily couple with the compound having another functional group, eg. compounds having a protected SH group.

An intermediate represented by structural formula (II) is a compound which may be obtained by introducing a thiol group protected with a protection group to the other terminal amino group of the intermediate represented by structural formula (I).

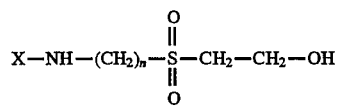
(II)

wherein n is an integral of one to four, X is one of

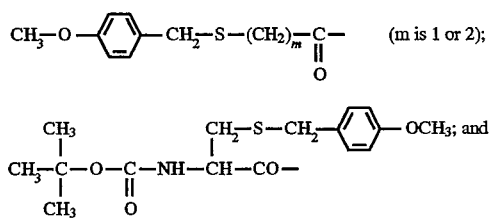

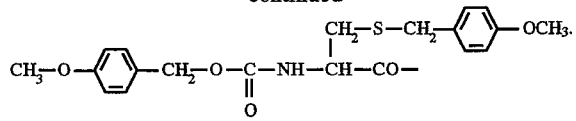

When the linker as mentioned above is added, as explained in FIG. 1, the linker will only couple with the mature target peptide, since only the mature peptide has the N-terminal amino group. Therefore, the active group included in the linker such as the SH group is introduced in the form of precursor to only the mature peptide at the other terminus thereof.

According to the conventional method, the deprotection reaction is effected under acidic conditions. The mature peptide coupled to the linker and the immature peptides end-capped, for example by an acetyl group, are cleaved from the solid-phase support. The linker is maintained stably bound to the N-terminus of the mature peptide in the deprotection reaction as explained before. When the compound represented by structural formula (III) is used as the linker, the p-methoxybenzyl group which is the protection group for the SH group of the linker is removed by the deprotecting reagent to allow the SH group to be exposed at the terminus. The ligand is then allowed to contact with the mixture of mature and immature peptides. The ligand is modified by a compound which has another functional group forming a stable bond with the functional group at the opposite terminus site of the linker immobilized thereon. In the case which contains an immobilized SH is the functional group, the ligand where iodo-substituted aliphatic carboxylic acid or bromo-substituted aliphatic carboxylic acid on its surface is used. Especially preferable is an iodo-substituted aliphatic carboxylic acid derivative shown by the following general formula:

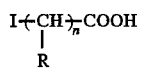

wherein R is H or an alkyl group of $C_1$ to $C_6$, n is an integer of one to six;

or a bromo-substituted aliphatic carboxylic acid derivative shown by the following general formula:

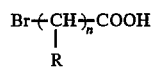

wherein R is H or an alkyl group of $C_1$ to $C_6$, n is an integer of one to six.

Derivatives of iodoacetic acid (I-CH$_2$COOH) or bromoacetic acid (BrCH$_2$COOH) are more preferred.

Specifically, a ligand having one of the structural formulae below is contacted with the peptide mixture under near neutral conditions:

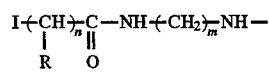

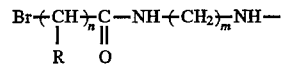

wherein R is H or an alkyl group of $C_1$ to $C_6$, n is 1 or 2 and m is 2 to 6.

Preferably the reaction is allowed to proceed at around pH=7 to 9 and in an inert buffer so as not to disturb the expected reaction. More preferably, a denaturing agent such as guanidine hydrochloride or urea is added in order to increase the solubility of the peptides.

As an example, 0.4M phosphate buffer or 0.4M tris (hydroxymethyl)aminomethane hydrochloride buffer (abbreviated as trishydrochloride buffer) is used. Guanidine hydrochloride of 4–7M, preferably ca0.6M guanidine hydrochloride, or urea of 4–8M, preferably ca0.6M urea is used as a denaturing agent. Other buffers and denaturing agents can be used on a case-by-case basis.

A solid-phase support, especially a hydrophilic solid-phase support, is the preferred ligand to which a compound having functional groups is immobilized. Kieselguhr ligand (solid-phase support beads) to which a suitable hydrophilic solid-phase support is absorbed so that it is usable in an aqueous system is shown as an example.

By the above process, the selective immobilization of the mature peptide to the ligand can be attained. The ligand is washed to remove immature peptides which do not bond to the ligand and to remove scavengers used for deprotection. The mature peptide is finally cleaved from the linker-bound ligand under conditions to selectively cleave the bond between the linker and the mature peptide. For example, the mature peptide is cleaved from the linker-bound ligand under a basic condition, if the linker is a compound shown by structural formula (III). If 5% ammonium solution is used for this basic treatment, some peptides which are not dissolved in 5% NH$_4$OH may remain as precipitates in the column. If the 5% ammonium treatment is followed by an additional washing process with 50% acetic acid, the precipitates can be eluted from the column and recovered effectively. The washing of the ligand with acetic acid following the base treatment is also preferable from the view-point that ammonia is neutralized and may be sublimed by freeze-drying. The compound finally obtained is the mature peptide alone.

Figure 2:
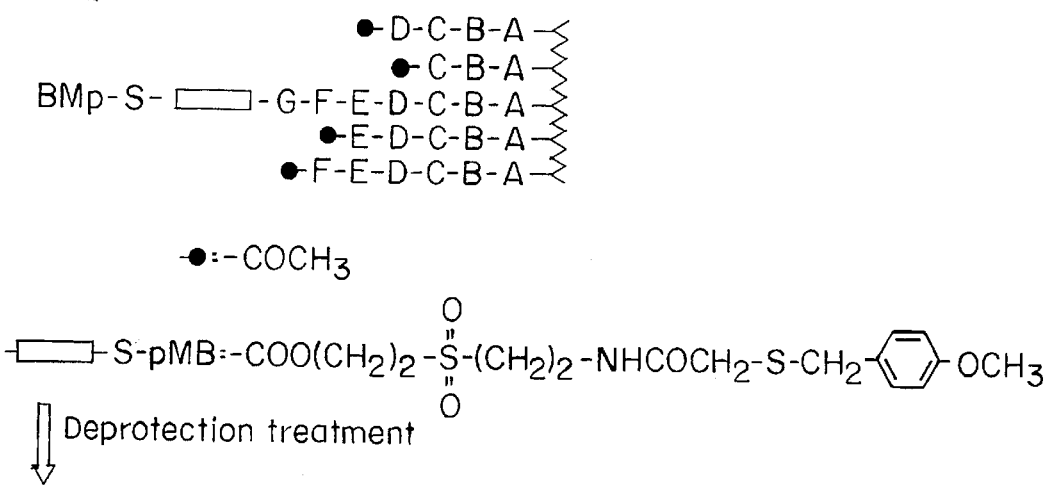
FIG. 2 is a flow chart showing synthesis of a peptide, binding of the linker and purification process of bonding of linker, and purification using a linker-bound ligands.
Figure 2:
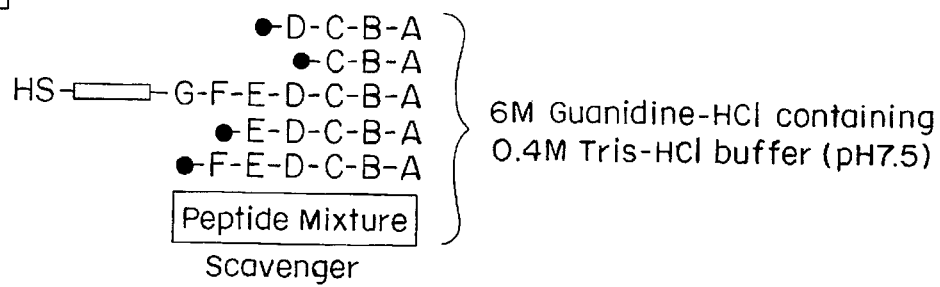
Figure 2:
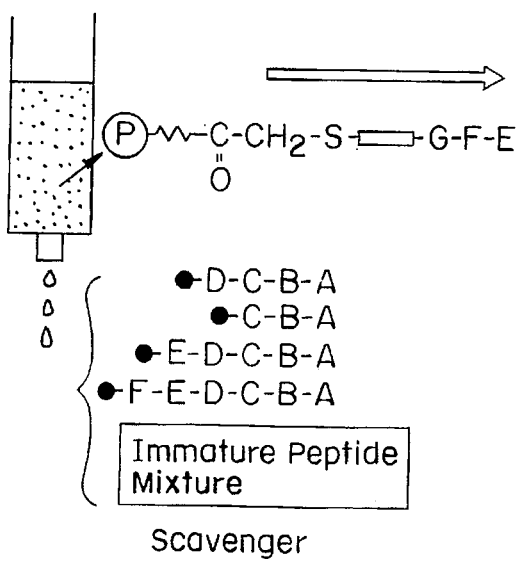
Figure 2:
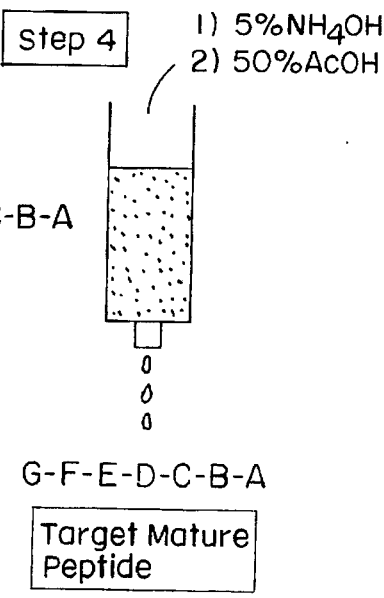

FIG. 2 is a flow-chart showing one embodiment of the peptide purification method of the present invention. In this figure the mature target peptide is shown as A-B-C-D-E-F-G, and A-B-C, A-B-C-D, A-B-C-D-E, and A-B-C-D-E-F are impurities. Step 1 of FIG. 2 shows the targeted mature peptide mixed with many impurities. Both the mature peptide having an N-terminal amino group and immature peptides (impurities) having an acetyl-group modified terminus (produced by end-capping with acetic anhydride) are bound to the solid-phase support (solid-phase support beads). The linker of the present invention is added to the solid-phase support, and the linker selectively bonds to the terminus of the mature peptide A-B-C-D-E-F-G alone. The final deprotection treatment in the peptide synthesis method cleaves the target peptide and immature peptides from the solid-phase support, as shown in step 2. This treatment allows the formation of an active functional group (SH group) at the other end of the linker bound to the target peptide. In step 3 the mixture of the mature peptide and immature peptides is contacted with a ligand of this invention packed in a column that can bond to the linker. The ligand bonds to the mature peptide alone via the linker, and immature peptides and other reagents are eluted from the column. Step 4 involves exposuring the column to basic condition under which the urethane bond between the linker and the mature peptide is selectively cleaved. This results in the cleavage of the mature peptide from the linker-bound ligand and the elution of the mature peptide from the column.

EXAMPLES

The present invention is described in more detail below by the following non-limiting examples.

Example I: Synthesis of the linker (A)

Figure 3:
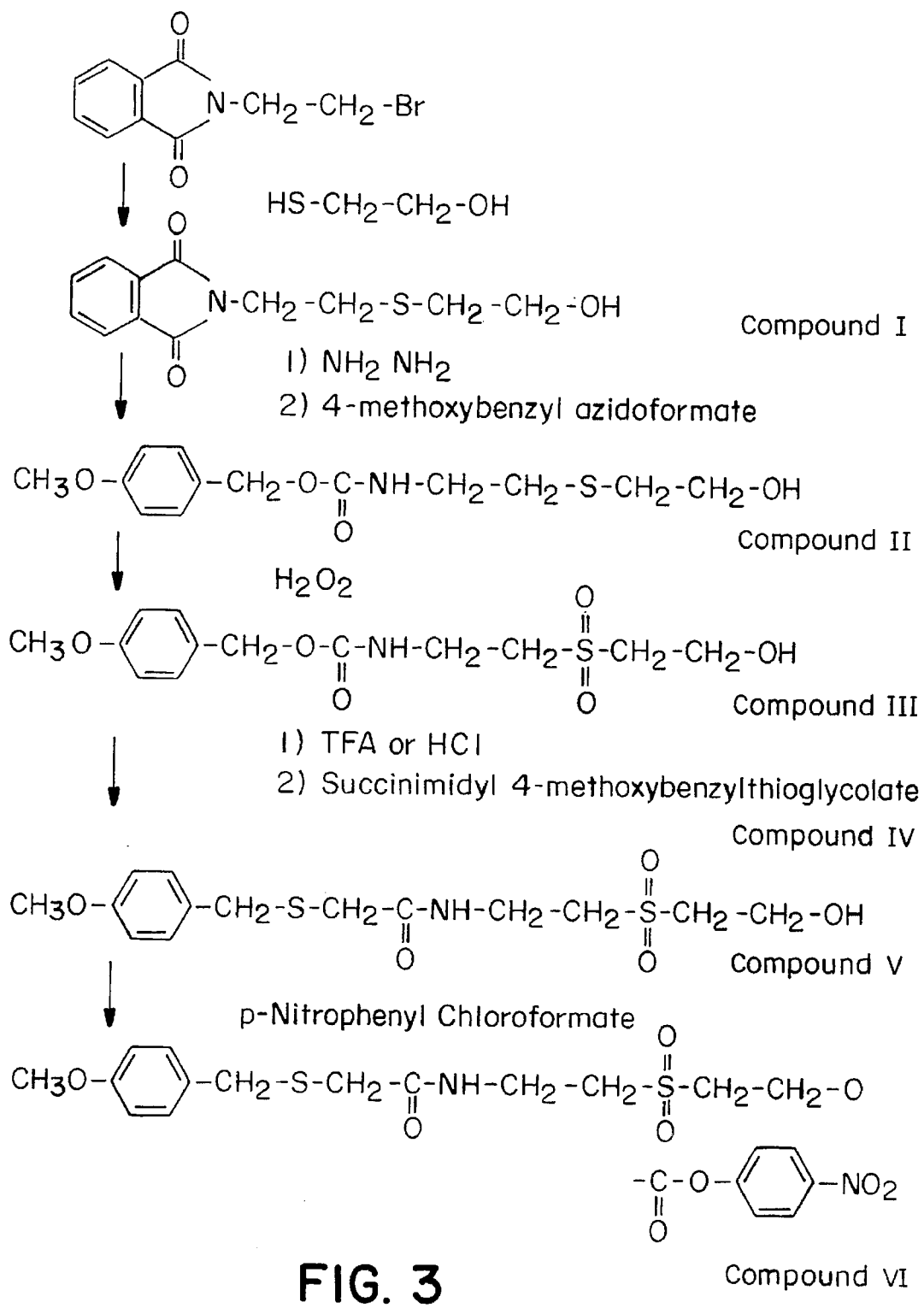
FIG. 3 is a flow chart showing reaction pathway for synthesis of the linkers.

This example describes a method for synthesizing linker, where the synthesis is performed according to steps shown in FIG. 3

1-1 Synthesis of the Compound (I)

Compound (I):2-[-(N-Phthaloyl)ethylthio]ethanol

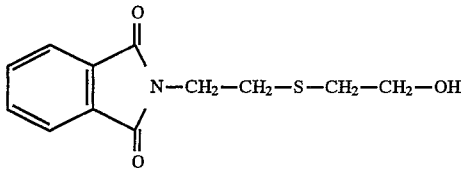

N-(2-Bromoethyl)phthalimide (50.8 g, 0.2 mol) and β-mercaptoethanol (14.3 ml, 0.2 mol) were dissolved in dimethylformamide (400 ml). After the further addition of dicyclohexylamine (39.9 ml, 0.2 mol) under cooling by ice, the solution was stirred for 4 hr. at room temperature. The produced salt (dicyclohexylamine hydrobromide) was removed by filtration. The filtrate was mixed with the washing solution that was obtained by the washing of the salt with a small amount of dimethylformamide. It was followed by the evaporation of the dimethylformamide under reduced pressure. The residue was dissolved in ethyl acetate and transferred to a separatory funnel. The ethyl acetate phase was washed with saturated brine three times. The ethyl acetate phase, being transferred to a Mayer's flask, was dried over anhydrous sodium sulfate. Subsequent to the removal of sodium sulfate by filtration, ethyl acetate was evaporated under reduced pressure to obtain 45.9 g of oily white compound (yield 91%).

1-2 Synthesis of Compound (II)

Compound (II): 2-[2-(4-Methoxybenzyloxycarbonylamino) ethylthio]ethanol

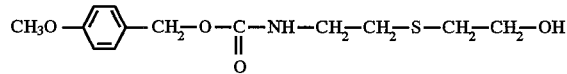

Compound I (43.5 g, 0.17 mol) obtained by the above procedure was dissolved in methanol (250 ml). The solution was stirred for 16 hr. after the addition of hydrazine hydrate (9.3 ml, 0.18 mol). The produced crystals were removed by filtration. Methanol was evaporated under reduced pressure. The residue was crystallized by the addition of acetonitrile, followed by recrystallization from methanol/acetonitrile to obtain 45.9 g of white crystals (yield 86%). The crystals were dissolved in a mixture of water (100 ml) and triethylamine (23.6 ml).

The crystals were added to an acetonitrile solution (100 ml) of paramethoxybenzylazidoformate (34.7 g, 0.16 mol from Watanabe Chemical Kogyo Ltd.) under cooling by ice. The solution was then stirred for 10 hr. Subsequent to the evaporation of water/acetonitrile under reduced pressure, the oily residue was dissolved in ethyl acetate and transferred to a separatory funnel. The ethyl acetate phase was washed with 5% citric acid three times, followed by washing 3 times with saturated brine. After the ethyl acetate phase was transferred into a Mayer's flask, it was dried over anhydrous sodium sulfate. Subsequent to the removal of sodium sulfate by filtration, ethyl acetate was evaporated under reduced pressure. N-hexane was added to the residue to obtain crystals. The crystals were further recrystallized by ethyl acetate/n-hexane to obtain 37.12 g of white crystals (yield 93%).

The Specifications of Compound (II) above were as follows:

$Rf_1$=0.74

Melting point; 41°–41.5° C.

The theoretical values of $C_{13}H_{19}NO_4S$:

C=54.72; H=6.71; N=4.91

The measured values:

C=54.79; H=6.88; N=4.98

NMR (CDCl$_3$): δ 2.08(br.s,1H) 2.73–2.76 (m,4H), 3.39 (q,J=6. 1 Hz, 2H), 3.73 (t, J=5.7 Hz, 2H), 3.80 (s,3H), 5.04 (s, 2H), 5.12 (br. s, 1H) 6.88, 7.30 (AA' BB' pattern, $J_{ortho}$=8.8).

FAB Mass Spectroscopy: 286.1 (M+H$^+$)

(calculated on $C_{13}H_{19}NO_4S$: 285.1)

1-3 Synthesis of Compound (III)

Compound (III): 4-Methoxybenzyl 2-(2-hydroxyethylsulfonyl) ethylcarbamate aminoethylsulphonylethanol ethanol

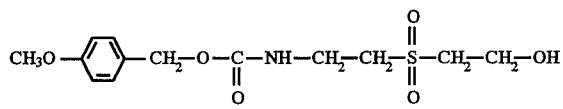

Compound II (18.2 g, 65 mmol) obtained by the above procedure was dissolved in water (100 ml) and methanol (100 ml). After the addition of sodium tungstenate (65 mg), hydrogen peroxide (16.3 ml, 114 ml/mol) was added dropwise to the solution while stirring. This was an exothermic reaction and the reaction temperature was controlled to 60° C. After the two-hour stirring, additional stirring was made with the addition of 5% palladium/carbon (0.5 g) until the foaming due to decomposition of excess hydrogen peroxide had ceased. 5% palladium/carbon was removed by filtration, and the solvent was evaporated under reduced pressure. The oily residue was dissolved in ethyl acetate and transferred to a separatory funnel. The ethyl acetate phase was washed with 5% citric acid three times, 5% sodium bicarbonate one time and saturated brine three times. After the ethyl acetate phase was transferred into a Mayer's flask, it was dried over anhydrous sodium sulfate. Subsequent to the removal of sodium sulfate by filtration, ethyl acetate was evaporated under reduced pressure. Diethyl ether was added to the oily residue to obtain crystals. The crystals were further recrystallized by ethyl acetate/diethyl ether to obtain 16.7 g of white crystals (yield 81%).

The specifications of Compound (III) obtained by the above were as follows:

$Rf_1$=0.52

Melting point 65°–66° C.

The theoretical values of $C_{13}H_{19}NO_6S$:

C=59.20; H=6.03; N=4.41

The measured values:

C=59.03; H=5.97; N=4.41

NMR (CDCl$_3$): δ 2.09(br.s,1H), 3.20 (t, J=5. 4 Hz, 2H), 3.34(t, J=5. 9 Hz, 2H), 3.72 (q, J=5. 9 Hz, 2H), 3.80 (s, 3H), 4.08 (t, J=5. 4 Hz, 2H), 5.04 (s, 2H), 5.46 (br. t like, 1H), 6.88, 7.29 (AA' BB' pattern, $J_{ortho}$=8.8).

FAB Mass Spectroscopy: 340.1 (M+Na$^+$)

(calculated on $C_{13}H_{19}NO_6SNa$: 340.1)

1-4: Synthesis of Compound IV

Compound IV: Succinimidyl 4-methoxybenzylthioglycolate

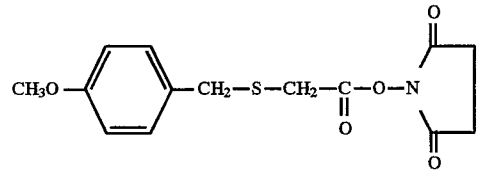

S-(p-methoxybenzyl)thioglycolic acid (1.49 g, 7 mmol) and 1-hydroxysucciimide (0.81 g, 7 mmol) were dissolved in tetrahydrofuran (10 ml). After the further addition of N,N'-dicyclohexylcarbodiimide (1.59 g, 7.7 mmol) with ice cooling, the solution was stirred for 5 hr. The resultant N,N'-dicyclohexylurea was separated by filtration, and tetrahydrofuran was evaporated under reduced pressure. Isopropyl alcohol was added to the residue to obtain crystals. The crystals were further recrystallized from tetrahydrofuran/iso-propyl alcohol to obtain 1.25 g of white crystals (yield 58%).

The specifications of compound (IV) obtained by the above were as follows:

$Rf_2$=0.86

Melting point 88°–89° C.

The theoretical values of $C_{14}H_{15}NO_5S$:

C=54.36; H=4.88; N=4.53

The measured values:

C=54.07; H=4.85; N=4.48

FAB Mass Spectroscopy: 332.1 (M+Na$^+$)

(calculated on $C_{14}H_{15}NO_5SNa$: 332.1)

1–5: Synthesis of Compound V

Compound V: N-[2-(2-Hydroxyethylsulfonyl)ethyl]-4-methoxybenzylthioacetamide

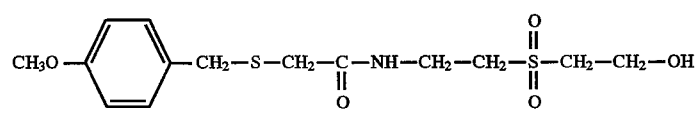

Compound III mentioned above (5.0 g, 15.8 mmol) was treated with trifluoroacetic acid (20 ml) for 60 min. under the presence of anisole (5 ml) with ice cooling. Trifluoroacetic acid was evaporated under reduced pressure. The residue was dissolved in diethyl ether to produce an oily residue. The oily residue dissolved in dimethylformamide (50 ml) with ice cooling was stirred for 12 hr. at room temperature after the addition of triethylamine (4.5 ml), N-hydroxybenzotriazole (2.42 g) and Compound IV (5.86 g, 19.0 mmol). Dimethylformamide was evaporated under reduced pressure to obtain an oily residue. The obtained oily residue was dissolved in ethyl acetate, and transferred a separatory funnel. The ethyl acetate phase was washed with 5% citric acid 3 times, 5% sodium bicarbonate 3 times, and saturated brine. The ethyl acetate phase was transferred into a Mayer's flask and dried over anhydrous sodium sulfate. The removal of anhydrous sodium sulfate by a filtration was followed by the evaporation of ethyl acetate under reduced pressure. The obtained oily residue was crystallized by the addition of diethyl ether, and the obtained crystals were recrystallized from ethyl acetate/diethyl ether to obtain 4.31 g of white crystals (yield 78%).

The specifications of compound (V) obtained by the above were as follows:

$Rf_1=0.61$

Melting point 73°–75° C.

The theoretical values of $C_{14}H_{21}NO_5S_2$:

C=48.40; H=6.09; N=4.03

C=48.40; H=6.09; N=4.03

The measured values:

C=48.60; H=6.29; N=4.11

NMR (CDCl$_3$): δ 2.29 (br.s,1H), 3.13 (s, 2H), 3.31–3.23 (m, 4H), 3.71 (s, 2H), 3.72 (q, J=6.0 Hz, 2H), 3.80 (s, 3H), 4.13 (t, J=5.2 Hz, 2H), 6.86, 7.22 (AA' BB' pattern, $J_{ortho}=$8.7) 7.31 (br. t like, 1H).

FAB Mass Spectroscopy: 348.1 (M+H$^+$)

(calculated on $C_{14}H_{21}NO_5S_2$: 347.1)

1-6: Synthesis of Compound VI (linker)

Compound VI: 2-[2-(4-Methoxybenzylthiomethylcarbonylamino)ethylsulfonyl] ethyl 4-nitrophenyl carbonate

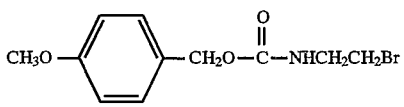

Hydrobromide of 2-bromoethylamine (100.0 g, 0.49 mol) was dissolved in tetrahydrofuran (THF 500 ml). After the further addition of para-methoxybenzylazido formate (111.2 g, 0.54 mol) and triethylamine (148.9 ml, 1.07 mol) under ice cooling, the solution was stirred for 10 hr. The produced salt (triethylamine hydrobromide) was removed by filtration. The filtrate was mixed with the washing solution that was obtained by the washing of the salt with a small amount of THF. The evaporation of THF under reduced pressure was followed. The residue was dissolved in ethyl acetate and transferred to a separatory funnel. Ethyl acetate phase was washed with 5% citric acid three times and with saturated brine three times. The ethyl acetate phase, being transferred to a Mayer's flask, was dried over anhydrous sodium sulfate. Subsequent to the removal of anhydrous sodium sulfate by filtration, ethyl acetate was evaporated under reduced pressure. The residue was crystallized by the addition of n-hexane followed by recrystallization from ethyl acetate/n-hexane to obtain 102.5 g of white crystals (yield 73%).

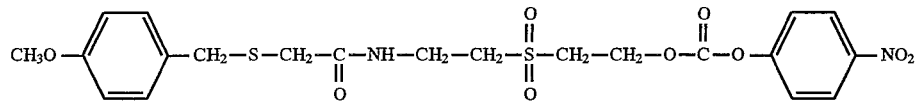

The compound V mentioned before (4.00 g, 11.5 mmol) was dissolved in anhydrous pyridine (30 ml). After the addition of para-Nitrophenyl chloroformate (2.32 g, 11.5 mmol) under ice cooling, the solution was stirred for 4 hr. Pyridine was evaporated under reduced pressure. The produced oily residue was crystallized by the addition of 1N hydrochloric acid (50 ml) and diethyl ether. The obtained crystals are recrystallized from hydrochloric acid/diethyl ether to obtain 4.07 g of white crystals (yield 69%).

The specifications of compound (VI) obtained by the above were as follows:

$Rf_2=0.37$

Melting point 81°–82° C.

The theoretical values of $C_{21}H_{24}N_2O_9S_2$:

C=49.21; H=4.72; N=5.47

The measured values:

C=49.30; H=4.72; N=5.25

NMR (CDCl$_3$): δ 3.13 (s, 2H), 3.28 (t, J=6.0 Hz, 2H), 3.47 (t, J=5.7 Hz, 2H), 3.75 (q, J=6.0 Hz, 2H), 3.79 (s, 3H), 4.74 (t, J=5.7 Hz, 2H), 6.84, 7.20 (AA' BB' pattern, $J_{ortho}=$8.7) 7.25 (m, 1H), 7.40, 8.28 (AA' BB' pattern, $J_{ortho}=$9.3).

FAB Mass Spectroscopy: 513.2 (M+H$^{3O}$)

(calculated on $C_{21}H_{24}N_2O_9S_2$: 512.1)

Example II: Synthesis of the Linker (B)

Figure 4:
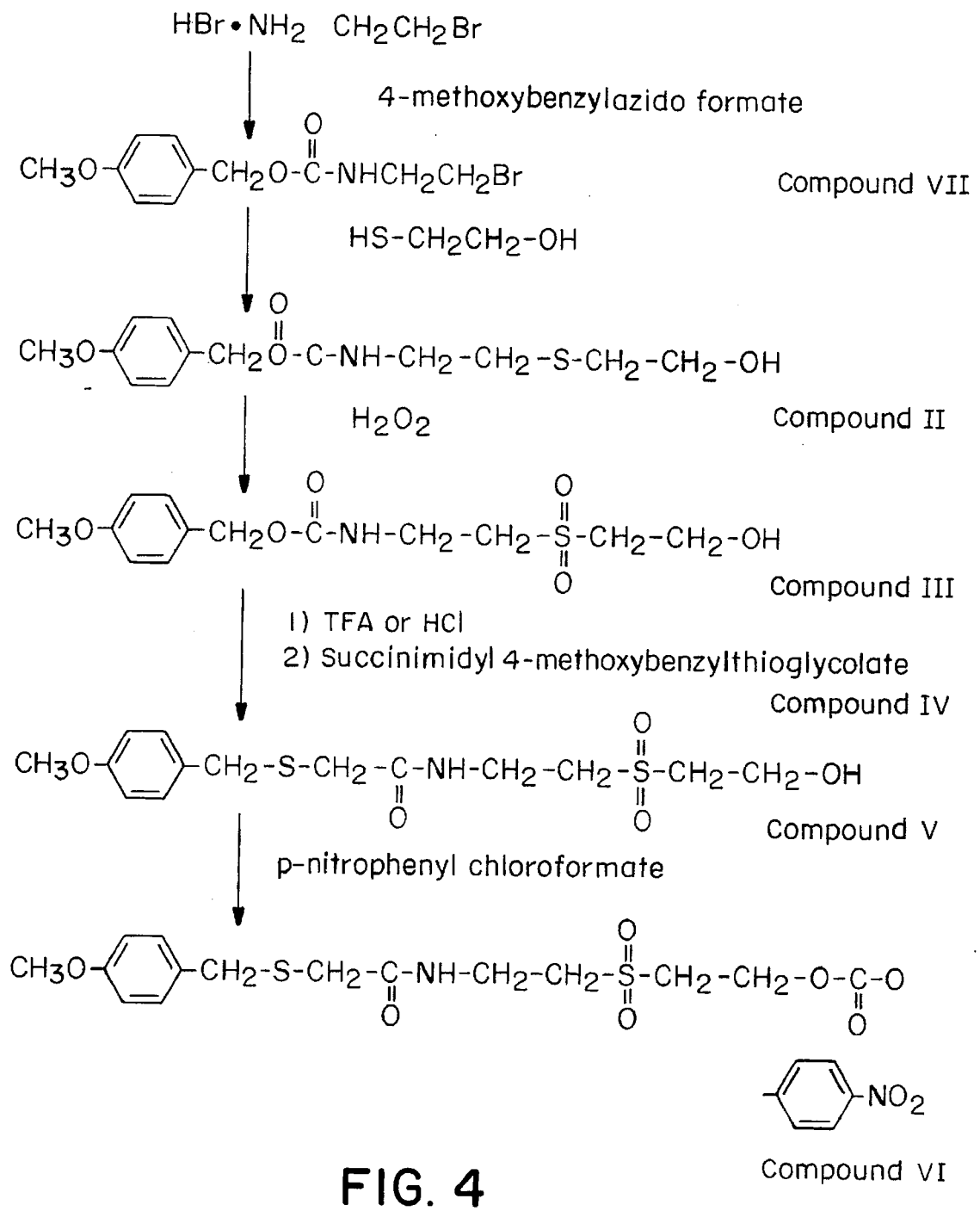
FIG. 4 is a flow chart showing another reaction pathway for synthesis of the linkers.

This example describes another synthesis of the linker, according to steps shown in FIG. 4.

2-1 Synthesis of the Compound (VII)

Compound (VII): 4-Methoxybenzyl 2-bromoethylcarbamate

The specifications of Compound (VII) above were as follows:

$Rf_4=0.3$

Melting point 44.5°–45.5° C.

The theoretical values of $C_{11}H_{14}NO_3Br$:

C=45.85; H=4.90; N=4.86

The measured values:

C=45.59; H=4.84; N=4.80

2—2 Synthesis of Compound (II)

Compound VII (100 g, 0.35 mol) obtained by the above method and β-mercaptoethanol (25.0 ml, 0.35 mol) were dissolved in dimethylformamide (DMF, 700 ml). After the further addition of dicyclohexylamine (70 ml, 0.35 mol) under ice cooling, the solution was stirred for 4 hr. at room temperature. The produced salt (dicyclohexylamine hydrobromide) was removed by filtration. The filtrate was mixed with washing solution obtained by the washing of the salt with a small amount of DMF. DMF was evaporated under reduced pressure. The residue dissolved in ethyl acetate, was transferred to a separatory funnel. The ethyl acetate phase was washed with 5% citric acid three times, and followed by saturated brine three times. The ethyl acetate phase was transferred to a Mayer's flask, and subsequently ethyl acetate was dried over anhydrous sodium sulfate. Subsequent to the removal of anhydrous sodium sulfate by filtration, ethyl acetate was evaporated under reduced pressure. N-hexane was added to the residue for crystallization. The obtained crystals were further recrystallized from ethyl acetate/n-hexane to obtain 90.5 g of white crystals (yield 91%). The melting point of compound II obtained was 41°–41.5° C.

2-3 Synthesis of Compound (VI) (linker)

Compound (III) was produced from Compound II, obtained as above, according to the procedure described in 1–3. Compound V was synthesized according to the procedure described in 1–5 and compound VI (linker) was produced according to the procedure in 1–6.

Example III: Synthesis of the Linker (C)

Figure 5:
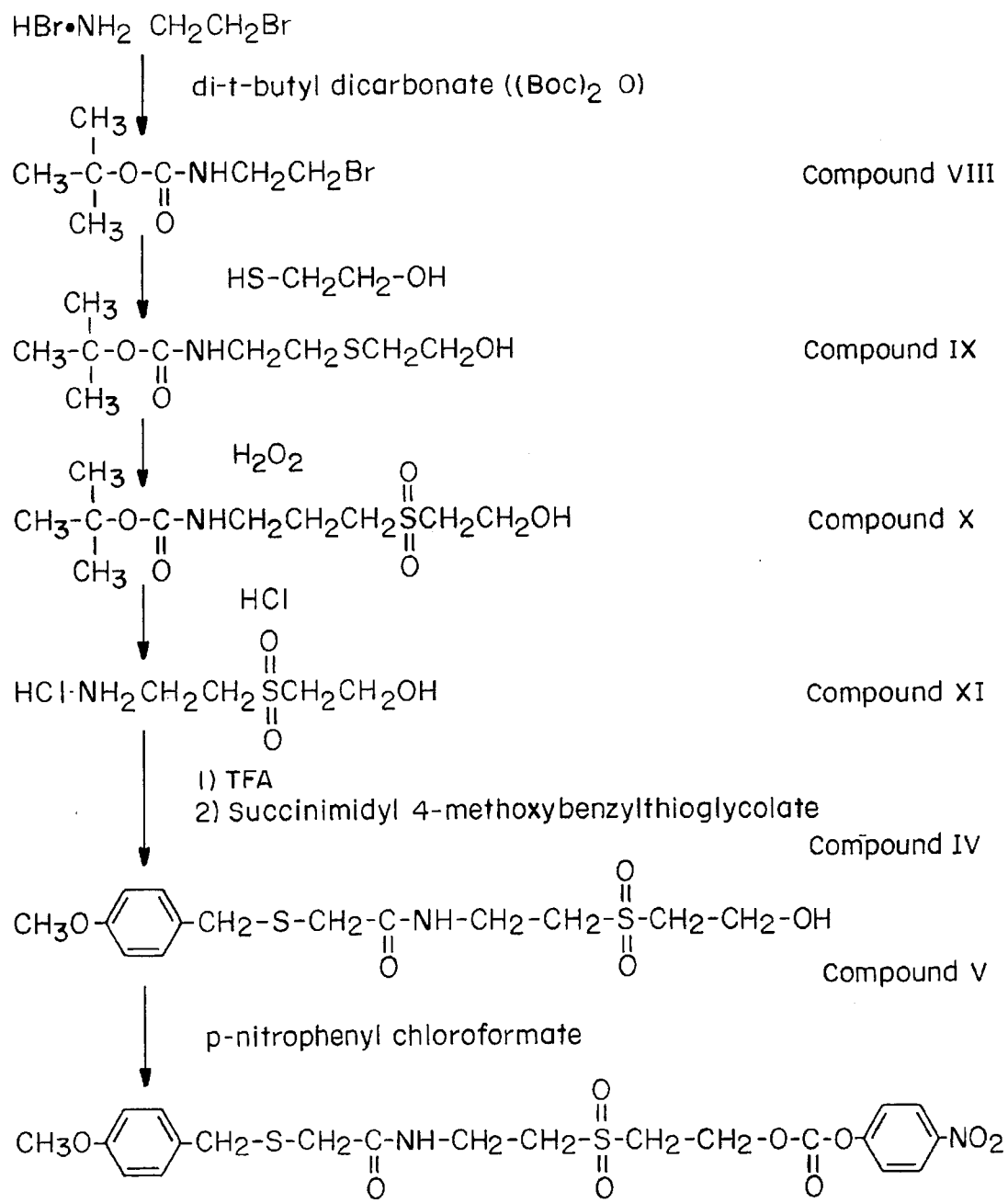
FIG. 5 is a flow chart showing other reaction pathway for synthesis of the linker.

This example describes another method for the synthesis of the linker, according to steps shown in FIG. 5.

3-1 Synthesis of the compound (VIII)

Compound (VIII): t-butyl 2-bromoethylcarbamate

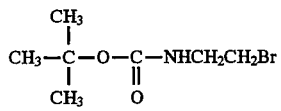

2-Bromoethylamine hydrobromide (10 g, 49 mmol) was dissolved in dimethylformamide (DMF 100 ml). After the further addition of di-t-butyldicarbonate ((Boc)$_2$O) (11.8 g, 54 mmol, 1.1 equivalent) and triethylamine (10.3 ml, 74 mmol, 1.5 equivalent) under ice cooling, the solution was stirred for 2 hr. at room temperature. The produced salt triethylamine hydrobromide) was removed by filtration. The filtrate was mixed with the solution obtained by washing the salt with a small amount of DMF. Rf$_2$ of this compound is 0.90.

3-2 Synthesis of Compound IX

Compound (IX): t-Butyl 2-(2-hydroxyethylthio) ethylcarbamate

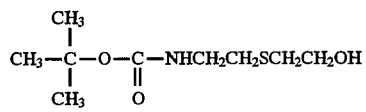

DMF solution (filtrate and washing solution) of Compound VIII (49 mmol) obtained above was mixed with β-mercaptoethanol (3.5 ml). After the further addition of dicyclohexylamine (9.8 ml, 49 mmol) under ice cooling the solution was stirred for 20 hr. at room temperature. The produced salt dicyclohexylamine hydrobromide) was removed by filtration. The filtrate was mixed with the solution obtained by the washing of the salt with DMF. DHF was evaporated under reduced pressure. The residue was dissolved in ethyl acetate, and the ethyl acetate solution was washed with 5% citric acid three times and with saturated brine three times. The washed ethyl acetate solution was dried over anhydrous sodium sulfate. Subsequent to the removal of anhydrous sodium sulfate by filtration, ethyl acetate was evaporated under reduced pressure to obtain a transparent oily compound (Compound IX).

3—3 Synthesis of Compound (X) Compound X: t-Butyl 2-(2-hydroxyethylsulfonyl)ethylcarbamate (oily compound)

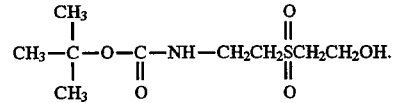

Compound (IX) (49 mmol) obtained by the procedure described in 3-2 was dissolved in methanol (85 ml). Water (40 ml) followed by sodium tungstate (49 mg) was added, and aqueous hydrogen peroxide (11.3 ml) was added dropwise with stirring of the solution. This was an exothermic reaction and the reaction temperature was controlled to remain below 60° C. After stirring for one-hour and a half 5% paladium/carbon (0.38 g) was added with additional stirring to decompose the excess hydrogen peroxide. The stirring was continued until the foaming had ceased. 5% paladium/carbon was removed by filtration, and the filtrate was evaporated under reduced pressure. The oily residue, dissolved in ethyl acetate, was washed with 5% citric acid three times, 5% sodium hydrogencarbonate one time and saturated brine three times. After the ethyl acetate phase was transferred to a Mayer's flask, it was dried over anhydrous sodium sulfate. Subsequent to the removal of anhydrous sodium sulfate by filtration, ethyl acetate was evaporated under reduced pressure 11.79 g of oily compound (compound X) was obtained.

3-4: Synthesis of Compound XI

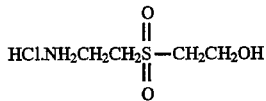

Compound XI: 2-(2-Hydroxycthylsulfonyl)ethylamine hydrochloride

Compound X (49 mmol) obtained by the procedure described above in 3—3 was dissolved in 4N-HCl/dioxane (40 ml) and stirred for 30-min. The obtained crystals were collected by filtration and washed with ether. The crystals were subsequently dried under vacuum. 6.6 g (35 mmol) of crystals (Compound XI) were obtained, and the yield was 71%.

Rf$_5$=0.45

Melting point 255° C.

The theoretical values of $C_4H_{12}NO_3SCl$:

C=25.33; H=6.38; N=7.39

The measured values:

C=25.24; H=6.50; N=7.43

3-5: Synthesis of Compound V

Compound V was synthesized from Compound XI, produced by the above method, according to the procedure described in 1-5.

3-6: Synthesis of Compound VI (linker)

Compound VI (linker) was synthesized from compound V mentioned above according to the procedure described in 1-6.

Example 4: Synthesis of Resin for bonding the Linker Synthesis of IodoAcetic Acid Resin Methylene chloride solution (50 ml) of iodoacetic acid (7.4 g, 40 mmol), where dicyclohexylcarbodiimide (5 g, 0.6eq.) was added, was stirred for 30 min. under ice cooling. The produced precipitate (dicyclehexylurea) was removed by filtration. The filtrate was treated with ethylenediamine. The treated filtrate was then added to PepSyn K resin* whose terminal aminoethyl group was attached (20 g, amino group content: 0.2 mmol/g), and shaken until a Kaiser test gave a negative result (2 hr). The resin was washed well with dimethylformamide and methylene chloride, and dried under vacuum.

*produced by Millipore Co., Ltd., Kieselgur type resin: copolymer of dimethylacrylamide, bis acroylethylenediamine and acryloylsarcosine methylester was supported by Kieselguhr.

Example 5: Purification of Synthesized Peptide (1)

Polyphemusin II was synthesized and purified in order to clarify the availability of this purification of the present invention. Polyphemusin II was synthesized by Fmoc-based solid-phase synthesis according to the procedure shown in FIG. 1, and purified. Polyphemusin II is a 18-residue peptide with C-terminus amide and two disulfide bonds. For the synthesis, cys derivative whose thiol group was protected with Acm (acetamido methyl) was used SEQ ID No:1:

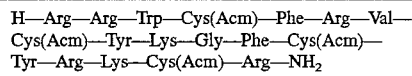

At the final step of the synthesis, linker prepared according to Example 1 (512 mg, 5 equivalent) and N-Hydroxybenzotriazole (152 mg, 5 equivalent) were added to the solid phase resin (0.2 mmol), and then stirred in dimethylformamide (10 ml) for 2 hr. In order to attach the linker to the N-terminus of Polyphemusin synthesized on the resin. Subsequently the deprotection of the solid phase resin was carried out at 0° C. for 2 hr. with a solution (10 ml) of 1M trimethylsilyl bromide (1.33 ml) (TMSBr)1M thioanisole (1.2 ml)/trifluoroacetic acid (6.97 ml) (TFA) in the presence of m-cresol (0.5 ml) [N. Fujii, A. Otaka, N. Sugiyama, M. Hatano, and H. Yajima, Chem. Pharm. Bull., 35, 3880]. TMSBr and TFA were evaporated off, and diethyl ether was added to obtain the peptide as a powder. The obtained powder was dissolved in 0.4M Tris hydrochloric acid buffer (pH7.5) containing 6M guanidine hydrochloride. Subsequently the solution was introduced onto a column packed with 1 equivalent of iodoacetic acid resin prepared by the procedure described in Example 4., and it was recirculated for 2 hr. to allow reaction. This was then treated with 1 equivalent of 2-mercaptoethanol for 2 hr. to inactivate iodoacetyl groups on the resin. The inactivated iodoacetic acid resin was washed well with 0.4M tris hydrochloric acid buffer (pH7.5) containing 6M guanidine hydrochloride, 50% acetic acid, and water sequentially.

The obtained peptide-bound resin was treated with 5% ammonium hydroxide solution for 30 min. to cleave the peptide from the resin. The resin was further washed with 50% acetic acid and the acetic acid washings were combined with the solution obtained from the ammonium hydroxide cleavage step. The obtained liquid was freeze-dried to obtain 14.2 mg of the peptide powder. Analysis by HPLC showed a single peak (purity: >99%).

The HPLC analysis of crude Polyphemusin II just after the solid-phase synthesis was approximately 69%, and a shoulder peak before the main peak was observed. However, the purified peptide obtained by the method of the present invention had a single peak. The results of amino acid sequence analysis and FAB mass spectroscopy of the purified peptide agreed with the theoretical [Acm-Polyphemusin II:2714.1 (M+H$^+$), calculated on $C_{120}H_{185}N_{41}O_{24}S_4$].

Example 6: Purification of Synthesized Peptide (2)

The present invention was used to synthesize human cholecystokinin, a small sized protein in order to further exemplify the feasibility of the purification procedure.

Human cholecystokinin was synthesized by Fmoc-based solid-phase synthesis according to the procedure shown in FIG. 1, and purified. Human cholecystokinin is a 33-residue peptide SEQ ID No:2:

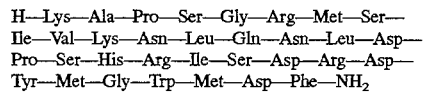

At the final step of the synthesis, the linker prepared according to Example 1 (512 mg, 5 equivalent) and N-Hydroxybenzotriazole (152 mg, 5 equivalent) were added to the solid phase resin (0.2 mmol), and subsequently stirred in dimethylformamide (10 ml) for 2 hr. in order to attach the linker to the N-terminus of human Cholecystokinin which was synthesized on the resin. Deprotection was carried out at 0° C. for 2 hr. by 1M TMSBr-thioanisole/trifluoroacetic acid (TFA) (10 ml) in the presence of ethanediol (0.2 ml) and m-cresol (0.5 ml). Following the deprotection, TMSBr and TFA were evaporated off, and diethylether was added to obtain the peptide as a powder. The obtained powder was dissolved in 0.4M Tris hydrochloric acid buffer (pH7.5) containing 6M guanidine hydrochloride. Subsequently the powder was introduced onto a column, where 1 equivalent of iodoacetic acid resin prepared by the procedure in Example 4 is packed, to allow recirculation for 2 hr. By the treatment with 1 equivalent of 2-mercaptoethanol of the resin for 2 hr., excess iodoacetic acid was deactivated. After removal of the solution from the column, the resin was washed well with 0.4M tris hydrochloric acid buffer (pH7.5) containing 6M guanidine hydrochloride, 50% acetic acid, and water sequentially.

The obtained peptide-bound resin (ligand) was treated with 5% ammonium hydroxide solution for 30 min. to cleave the peptide from the resin. After the further washing of the resin with 50% acetic acid, the wash solution was added to the above reagent for cleaving. The obtained liquid was freeze-dried to obtain 7.9 mg of the peptide powder. Analysis by HPLC showed a single peak (purity: more than 90%). The purity of human cholecystokinin which was produced in its sulfate free form was 29%, when calculated from crude peptide just after synthesis by the Fmoc method. The retention time by HPLC of non-sulphuric acid cholecystokinin purified by the method of this invention was identical to that purified by HPLC. The results of amino acid sequence analysis and FAB mass spectroscopy of the purified peptide agreed with the theoretical [:3865.2 (M+H$^+$), calculated on $C_{167}H_{263}N_{51}O_{49}S_3$].

Example 7: Purification of Synthesized Peptide (3)

The present invention was employed for the synthesis of another small sized protein, human Growth Hormone Releasing Factor (hGRF) represented by the following amino acid sequence SEQ ID No:3, in order to clarify the availability. hGRF was synthesized by Fmoc-based solid-phase synthesis according to the procedure shown in FIG. 1, and purified. hGRF is a 44-residue peptide.

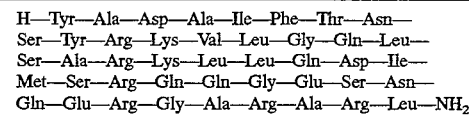

At the final step of the synthesis, the linker prepared according to Example 1 (512 mg, 5 equivalent) and N-hydroxybenzotriazole (152 mg, 5 equivalent) were added to the solid phase resin (0.2 mmol), and subsequently stirred in dimethylformamide (10 ml) for 2 hr. in order to attach the linker to the N-terminus of hGRF which was synthesized on the resin. Deprotection was carried out at 0° C. for 2 hr. with 1M TMSBr-thioanisole/trifluoroacetic acid (TFA) (10 ml) in the presence of ethanediol (0.2 ml) and m-cresol (0.5 ml). Following the deprotection, TMSBr and TFA were evaporated off, and diethylether was added to obtain the peptide as a powder. The obtained powder was dissolved in 0.4M Tris hydrochloric acid buffer (pH7.5) containing 6M guanidine hydrochloride. Subsequently the powder was introduced onto a column, where 1 equivalent of iodoacetic acid resin prepared In Example 4 was packed, to allow recirculation for 2 hr. By the treatment with 1 equivalent of 2-mercaptoethanol of the resin for 2 hr., excess iodoacetic acid resin was endcapped. After the removal of the solution from the column, the resin was washed well with 6M 0.5), 5.0% acetic acid, and water sequentially.

The obtained peptide-bound resin (ligand) was treated with 5% ammonium solution for 30 min. to cleave the peptide from the resin. After the further washing of the resin with 50% acetic acid, the wash solution was added to with reagent for cleaving. The obtained liquid was freeze-dried and 12.6 mg of the peptide powder was obtained. Analysis by HPLC showed almost a single peak (purity: more than 80%). The purity of hGRF was 51%, when calculated from crude peptide Just after synthesis by the Fmoc method. The retention time by HPLC of hGRF purified by the method of this invention was identical to that purified by HPLC.

The results of amino acid sequence analysis and FAB mass spectroscopy of the purified peptide agreed with the theoretical [5037.8 $(M+H^+)$, calculated on $C_{215}H_{358}N_{72}O_{66}S$].

Instruments and reagents used for assay of the above examples are as follows:

Thin Layer Chromatography
Sorbent: silica gel G (Kiesel gel G, E. Merck, Germany)
Solvents:
$Rf_1$: Lower phase of $CHCl_3$-MeOH-$H_2O$ (8:3:1)
$Rf_2$: $CHCl_3$-MeOH (10:0.5)
$Rf_3$: $CHCl_3$-AcOH (19:1)
$Rf_4$: $CHCl_3$-Cyclohexane (2:1)
$Rf_5$: n-BuOH-AcOH-Pyridine-$H_2O$ (4:1:1:2)

Nuclear Magnetic Resonance
Bruker AC-300 spectorometer (Bruker Co., Ltd.)
Inner standard: tetramethylsilane FAB Mass Spectrocopy
ZAB SE Mass spectrometer (U.G. Analytical)

Purity Analysis of Peptide
1) High Performance Liquid Chromatograph (HPLC)
HPLC system Model 600E (Millipore Corp.)
μ-Bondasphere 5C18 column (Millipore Corp.) with solvent system of water (0.1% trifluoroacetic acid)- acetonitrile
2) Amino acid sequence of peptides Peptide sequencer Model 431A (Applied Biosystems Co.) and protein sequencer Model 6600 (Millipore Corp.)

Synthesis of model Peptides
Fmoc peptide synthesis by automated peptide synthesizer Model 9050 (Millipore Corp.)

Although foregoing invention has been described by way of illustration and example for purposes of clarity and understanding, it will be obvious that certain changes and modifications may be practiced within the scope of the invention, as limited only by the appended claims.

---

We claim:

1. A method for purifying a peptide produced by solid-phase synthesis, said method comprising the steps of:

a) obtaining a mixture of mature peptides having a free N-terminus amino group and immature end-capped peptides, wherein the peptides are covalently bound to a solid-phase support;

b) contacting the mixture of step (a) with a linker comprising:
      (i) a first functional group at one terminus of the linker having the structure —$SO_2$—$CH_2$—$CH_2$—P, wherein P is an activated carbonate group capable of reacting with the free N-terminal amino group to form a urethane linkage between the linker and the N-terminal amino group, wherein the urethane linkage between the linker and the N-terminal amino group is cleavable upon alkaline conditions but stable under acidic conditions;
      (ii) a functional group at the other terminus of the linker which has a protected thiol, wherein the protecting group is acid-labile,
         whereby the free N-terminal amino group of the mature peptide selectively reacts with the activated carbonate to form a urethane linkage between the linker and the N-terminal amino group of the mature peptide;

c) subjecting the mixture obtained from step (b) to strong acid to cleave the protecting group from the thiol to yield a free thiol and to cleave the peptides from the solid-phase support;

d) contacting the product of step (c) with a solid support-bound ligand that is capable of forming a stable covalent bond with the free SH on the linker, thereby forming a stable covalent bond between the solid phase ligand and the free thiol on the linker, thereby selectively binding the mature peptides via the free thiol and removing unbound peptides therefrom; and e) cleaving the urethane linkage between the linker and the N-terminal amino group under alkaline conditions.

2. The method of claim 1 wherein said linker has chemical structure (III):

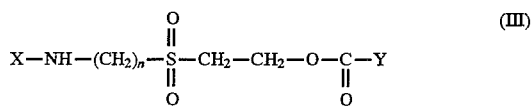

(III)

wherein n is an integer from one to four, X is one of

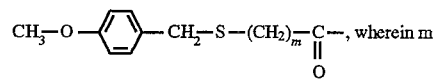

represents an integer of one or two;

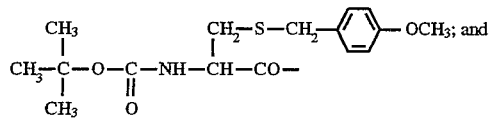

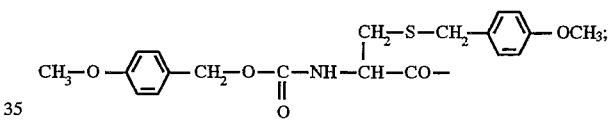

Y is one of

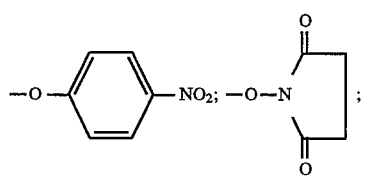

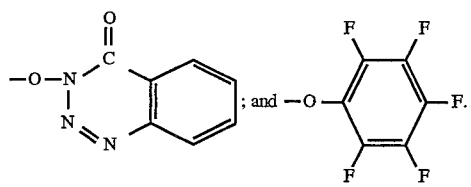

3. The method of claim 1 wherein said ligand has a compound immobilized thereon wherein said compound has the following structural formula:

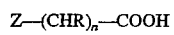

wherein:
   Z is Br or I;
   n is an integer from 1 to 6; and
   each R is independently H or a $C_1$ to $C_6$ alkyl group.

4. The method of claim 1 wherein said ligand has the following structural formula:

wherein:

Z is Br or I;

n is an integer from 1 to 6;

each R is independently H or a $C_1$ to $C_6$ alkyl group; and m is an integer from 2 to 6.

5. The method of claim 1 wherein said ligand comprises an iodo-aliphatic carboxylic acid or a bromo-aliphatic carboxylic acid, and wherein said ligand is immobilized on a hydrophilic surface.

6. The method of claim 1 wherein said ligand comprises an iodo-aliphatic carboxylic acid or a bromo-aliphatic carboxylic acid, and wherein said ligand is immobilized on a hydrophilic polymer absorbed on a Kieselguhr support.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Arg Arg Trp Cys Phe Arg Val Cys Tyr Lys Gly Phe Cys Tyr Arg Lys
1               5                   10                  15
Cys Arg
```

( 2 ) INFORMATION FOR SEQ ID NO:2:

( i ) SEQUENCE CHARACTERISTICS:
( A ) LENGTH: 33 amino acids
( B ) TYPE: amino acid
( D ) TOPOLOGY: linear ( i i ) MOLECULE TYPE: peptide ( x i ) SEQUENCE DESCRIPTION: SEQ ID NO:2:

```
Lys Ala Pro Ser Gly Arg Met Ser Ile Val Lys Asn Leu Gln Asn Leu
1               5                   10                  15

Asp Pro Ser His Arg Ile Ser Asp Arg Asp Tyr Met Gly Trp Met Asp
                20                  25                  30

Phe
```

( 2 ) INFORMATION FOR SEQ ID NO:3:

(i) SEQUENCE CHARACTERISTICS:
    (A) LENGTH: 44 amino acids
    (B) TYPE: amino acid
    (D) TOPOLOGY: linear (ii) MOLECULE TYPE: peptide (xi) SEQUENCE DESCRIPTION: SEQ ID NO:3:

| Tyr | Ala | Asp | Ala | Ile | Phe | Thr | Asn | Ser | Tyr | Arg | Lys | Val | Leu | Gly | Gln |
|---|---|---|---|---|---|---|---|---|---|---|---|---|---|---|---|
| 1 | | | | 5 | | | | | 10 | | | | | 15 | |
| Leu | Ser | Ala | Arg | Lys | Leu | Leu | Gln | Asp | Ile | Met | Ser | Arg | Gln | Gln | Gly |
| | | | 20 | | | | | 25 | | | | | 30 | | |
| Glu | Ser | Asn | Gln | Glu | Arg | Gly | Ala | Arg | Ala | Arg | Leu | | | | |
| | | 35 | | | | | 40 | | | | | | | | |